United States Patent [19]

Lin et al.

[11] Patent Number: 5,304,479
[45] Date of Patent: Apr. 19, 1994

[54] PHENCYCLIDINE COMPOUNDS AND ASSAYS FOR ITS DETERMINATION

[75] Inventors: Cheng-I Lin, Cupertino; Yuh-geng Tsay, Los Altos Hills, both of Calif.

[73] Assignee: Diagnostic Reagents, Inc., Santa Clara, Calif.

[21] Appl. No.: 803,057

[22] Filed: Dec. 6, 1991

[51] Int. Cl.$^5$ ............... C12N 9/96; C07K 17/06; C07D 211/06
[52] U.S. Cl. ................... 435/188; 530/350; 530/807; 546/205; 436/901; 436/816
[58] Field of Search ............ 435/188; 530/350, 807; 546/205; 436/901, 816

[56] References Cited

U.S. PATENT DOCUMENTS

| | | | |
|---|---|---|---|
| 3,875,011 | 4/1975 | Rubenstein et al. | 195/99 |
| 3,878,187 | 4/1975 | Schneider et al. | 530/363 |
| 3,884,898 | 5/1975 | Schneider | 530/363 |
| 4,067,774 | 1/1978 | Rubenstein et al. | 195/63 |
| 4,196,185 | 4/1980 | Forella et al. | 436/539 |
| 4,281,065 | 7/1981 | Lin et al. | 435/188 |
| 4,446,065 | 5/1984 | Lin et al. | 530/389.8 |
| 4,868,132 | 9/1989 | Byrnes et al. | 436/546 |
| 5,155,212 | 10/1992 | Dubler et al. | 530/380 |

FOREIGN PATENT DOCUMENTS 0386644  9/1990  European Pat. Off. .

OTHER PUBLICATIONS

Owens et al., (1988) in *Chem. Abst.*, 110(19), 65, Abst #165983.
Gole et al., (1988) in *Chem Abst* 110, 183, Abst #226682.
Leighty et al., (1980) *Res Commun. Subst. Abuse*, 1(2), 139–149, in *Chem Abst.*, 93(23), 10, Abst #215215.
Kalir et al., (1976) *Isr. J. Chem.* 13(2), 125–136, in *Chem Abst.*, 85, 16, Abst. #13673.
Vincent et al., (1979) *Proc. Natl. Acad. Sci. USA*, 76(9), 4678–4682.
Vignon et al., (1982) *Eur. J. Pharm.*, 81, 531–542.
Woodworth et al., (1986) *J. Pharm. Exp. Ther.*, 238, 900–904.
Owens et al., (1988) *J. Pharm. Exp. Ther.*, 246, 472–478.
Inami et al., (Jun. 1991) *Chem. Pharm. Bull.* 39(6), 1426–1429.
Iorio et al., (Aug. 1991) *J. Med. Chem.*, 34(8), 2615–2623.
Deutsch et al., (1984) *J. Neurochem.* 42(2), 407–411 in *Chem. Abst.* 100(3), 64, Abst #96596.

*Primary Examiner*—David M. Naff
*Assistant Examiner*—Jon P. Weber
*Attorney, Agent, or Firm*—Oblon, Spivak, McClelland, Maier & Neustadt

[57] ABSTRACT

Novel derivatives of phencyclidine are provided as precursors for conjugating to antigenic proteins for the preparation of antibodies which bind to phencyclidine or conjugation to enzymes for use as reagents in immunoassays. The combination of the antibodies and enzyme conjugates provide a sensitive and rapid assay for phencyclidine.

23 Claims, No Drawings

PHENCYCLIDINE COMPOUNDS AND ASSAYS FOR ITS DETERMINATION

BACKGROUND OF THE INVENTION

1. Field of the Invention

The present invention is directed to novel phencyclidine compounds and conjugates of these compounds to proteins.

2. Discussion of the Background 1-(1'-phenylcyclohexyl)piperidine, otherwise known as phencyclidine, PCP, was originally used as an analgesic anaesthetic drug (pain-killing) for humans. It is now legally used exclusively as an animal tranquilizer due to its strong side effects, such as euphoria and hallucinations. Probably because of these side effects, PCP has become prevalent in the illicit drug market. It is often sold as "peace pill", "angel dust", "dust", "crystal", or "supergrass".

PCP is a dangerous and potent drug with lethal potential and has become a major drug abuse problem. Thus it is desirable that there be a simple accurate rapid technique for detecting the presence of PCP in physiological fluids, such as blood serum, urine and saliva.

There have been difficulties in attempting to identify PCP in physiological fluids. In one investigation (D. C. K. Lin et al., Biochem. Mass Spec., 206 (1975)) of urine from patients intoxicated by PCP, no metabolites were detected in untreated urine. However, two urinary metabolites were freed from conjugates by enzymatic hydrolysis and identified as 4-phenyl-4-piperidinocyclohexanol and 1-(1-phenylcyclohexyl)-4-hydroxypiperidine. An additional metabolite, tentatively identified as 1-phenyl-(4-hydroxycarboxyl)-4-hydroxypiperidine, was found in the urine of the rhesus monkeys after administration of PCP.

U.S. Pat. No. 4,281,065 discloses PCP conjugates to antigenic proteins and to enzymes. The conjugates are formed by bonding poly(amino acids) to the phenyl group of PCP.

U.S. Pat. No. 4,446,065 discloses oxime derivatives of PCP in which the cyclohexyl group of PCP is derivatized. The oxime derivatives are used to form protein conjugates useful in assays for PCP determinations.

SUMMARY OF THE INVENTION

One object of the present invention is to provide novel phencyclidine derivatives, antigenic protein conjugates of these derivatives for antibody production and enzyme conjugates of these derivatives for immunoassay applications.

This and other objects which will become apparent from the following specification have been achieved by the present PCP derivatives having the formula shown below:

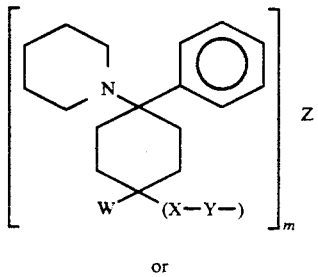

or

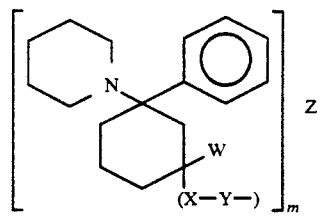

wherein

Y is a bond or a linking group,

X is $(CH_2)_a$ wherein $a = 1-10$; NR wherein is H, $C_{1-6}$ alkyl or said linking group Y; O; or S;

W is H, $C_{1-8}$ alkyl, or the group (X-Y-);

Z, hydrogen, hydroxy, $C_{1-6}$ alkoxy, an oxy group forming an activated ester capable of amide formation in aqueous medium or is a poly(amino acid) bonded to X or linking group Y; and m is 1 when Z is hydrogen, hydroxy, alkoxy or said oxy group and m is an integer from 1 to the molecular weight of Z divided by 500 when Z is a poly(amino acid).

DETAILED DESCRIPTION OF THE PREFERRED EMBODIMENTS

The PCP derivatives of the present invention are prepared by derivatizing the cyclohexyl ring of PCP and then bonding the derivatized PCP to a protein. The present PCP derivatives provide a means for conjugating PCP to antigenic proteins or to enzymes for immunoassay applications in a manner which does not alter the conformational structure of PCP. The compounds of the present invention, therefore, are superior phencyclidine derivatives for conjugation to proteins as compared to the oxime derivatives of U.S. Pat. No. 4,446,065 in which the oxime carbon-nitrogen double bond alters the normal conformation of the cyclohexyl ring of PCP.

The PCP derivatives of the present invention have the structure shown below:

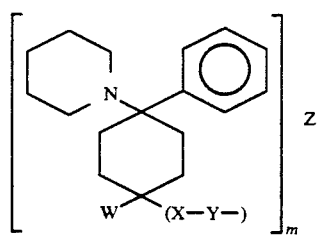

or

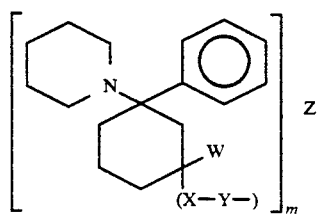

where Y is a direct covalent bond between X and Z or is a linking group. When Y is a linking group, the linking group is a functional group which is capable of linking the PCP derivative to a functional group present on poly(amino acid) Z. Suitable linking groups and methods of preparing the same are disclosed in U.S. Pat. No. 3,975,237, which is incorporated herein by reference. The functional groups which will be present in the poly(amino acid) and which may be used for linking to the PCP derivative include amino, guanidino, hydroxy, carboxy, mercapto, imidazole and activated aromatic groups, for example. These groups are present on the amino acid subunits which make up the poly(amino acid).

Amino acids having amino groups available for bonding to the linking group Y include lysine, arginine and histidine. Amino acids with free hydroxyl groups include serine, hydroxyproline, tyrosine and threonine. Amino acids which have free carboxyl groups include aspartic acid and glutamic acid. An amino acid having an available mercapto group is cysteine. Amino acids having activated aromatic groups include tyrosine and tryptophan. Preferably, an amino group on the poly(amino acid) will be bonded to linking group Y.

Linking group Y will generally have 1-14 carbon atoms, preferably about 2-8 carbon atoms and may be straight-chain or branched, saturated or unsaturated or have a cyclic structure. Where cyclic structures are involved, the cyclic structure is equated to the number of atoms providing a similar length straight chain structure. The total number of atoms in the linking group Y is 1 to about 30 atoms, generally 4 to about 20 atoms, including carbon, hydrogen, nitrogen, oxygen, phosphorous and sulfur atoms.

Preferably, the linking group will contain from 0 to 14 carbon atoms, preferably 2 to 8 carbon atoms and from 1 to 8 heteroatoms, where the heteroatoms are usually oxygen, sulfur and nitrogen, preferably oxygen and nitrogen. Examples of such linking groups include carbonyl, ester, thiocarbonyl, amide, urethane, carbamate, thiocarbamate, thiourethane, diazo and oxy groups. Specific examples for linking group Y include, but are not limited to, —C(O)—O—, —O—C-(O)—NR— (wherein R is H, straight-chain or branched $C_{1-10}$ alkyl, or alkylene when R is divalent as indicated below), —O—C(O)—, —NR—C(O)—, —C(S)—S—, —S—C(S)—, —C(O)—R—C(O)—, —C(O)—N-R—R—C(O)—, —P(P)(OR)—, —P(O)(R)—, —C-(O)—R—, —C(O)—R—S—, —C(S)—R—C(S)—, —C(S)—NH—R—C(S)—, —SO$_2$—, —SO—, —O—R—C(O)—, —S—R—C(O)—, —NR—R—, —O—R—, —O—R—C(S)—, —O—R—C(O)—, —N-R—R—C(S)—, —NR—R—C(O)—, —R—N$_2$, —N-$_2$—R—, —O—R—N$_2$—, and —NR—R—N$_2$—. When X is (CH$_2$)$_a$, linking group Y will generally have a carbonyl, thiocarbonyl NR, O or S bonded to X. When X is O, S or NR, linking group Y will generally have a carbonyl or thiocarbonyl group bonded to X. Any linking group capable of forming a stable covalent bond linkage between the PCP derivative and the poly(amino acid) in addition to these specifically identified linking groups is considered to be an equivalent to the above described linking groups and within the scope of the present invention.

The linking group Y is selected so that it is stable under the conditions of the immunoassay and when injected into an animal to produce antibodies thereto. When bonding the PCP derivative through the linking group Y to an enzyme for use in an immunoassay, the enzyme should retain at least a portion of its enzymatic activity. Further, the enzyme, i.e., poly(amino acid), must not prevent binding of an antibody to the PCP derivative.

The linking groups described above are well known organic functional groups, and the formation of the group —(X—Y—) on the PCP derivative can be accomplished with well known organic synthetic reactions. For example, if the PCP has an amino substituent, the amino group may be bonded to form an α-bromoacetamide. A displacement reaction on the α-bromo atom using a free amino or hydroxyl group on the poly(amino acid) will provide the linking group —C(O)—CH$_2$— between the amino group on the PCP and the amino or hydroxyl group on the poly(amino acid).

The derivatives of the present invention can be prepared from commercially available materials, such as 1,4-cyclohexanedione monoethyleneketal, piperidine hydrochloride, ethyl isocyanatoacetate and phenylmagnesium bromide, as described below.

Numerous PCP derivatives are available through 4-phenyl-4-piperidino-cyclohexanone (PPCH). Reaction of PPCH with an appropriate $C_{1-8}$ alkyl or alkylester triphenyl phosphonium halide using a Wittig or Wittig-Horner reaction results in the corresponding alkylidene or alkylidene ester at the 3- or 4-position of the cyclohexane ring. The alkene may then be reduced to a saturated alkylene group or may be subjected to an addition reaction, for example by addition of a mercapto or alcohol reagent to the carbon-carbon double bond. Addition reactions occur with the nucleophile adding to either the ring carbon or the exocyclic carbon of the carbon-carbon double bond. Mixtures are frequently obtained and may be separated by conventional chromatographic methods. Addition of the oxygen or sulfur atom of the alcohol or mercapto compound to the ring carbon produces compounds in which W is a $C_{1-8}$ alkyl group. Addition of the oxygen or sulfur atom to the exocyclic carbon produces compounds in which W is hydrogen.

The carbonyl of PPCH also enables the formation of ketal and thioketal compounds where W is (X—Y—) and X is O or S. The addition of two moles of an alcohol or mercapto compound to the carbonyl of PPCH produces the corresponding ketal or thioketal. Preferably, the alcohol or mercapto reagent will contain a further functional group such as a carboxylic acid, ester, amide, etc. which allows further bonding of the derivatized PCP to the poly(amino acid). Examples include reaction of PPCH with mercapto acetic acid, hydroxyacetic acid, etc.

The starting PPCH is prepared by reacting 1,4-cyclohexanedione monoethyleneketal with potassium cyanide and piperidine hydrochloride to form 4-cyano-4-piperidinocyclohexane ethylene ketal. This ketal is then reacted with phenyl magnesium bromide under anhydrous conditions to form the corresponding 4-phenyl-4-piperidino-cyclohexane ethylene ketal which is hydrolyzed to form the corresponding cyclohexanone derivative.

The carbonyl of PPCH may also be either reduced using a conventional reducing agent such as sodium borohydride to form the corresponding cyclohexanol derivative (X is O), reacted with aminooxyacetic acid hydrochloride to form the corresponding oxime or subjected to amination to form the corresponding amino derivative. Reduction of the oxime using catalytic hydrogenation or a suitable reducing agent such as sodium cyanoborohydride produces the amino derivative (X is NH).

The 4-phenyl-4-piperidino-cyclohexanol and 4-phenyl-4-piperidino-cyclohexylamine produced as described above, may then be reacted with a suitable $C_{1-6}$ alkyl isocyanato acetate to form the PCP-carbamate alkyl esters and PCP-urethane alkyl esters, respectively. These alkyl esters may be hydrolyzed to form the corresponding carboxylic acids which are then employed to form an activated ester capable of reacting with the amino groups of poly(amino acid) to form linking amide bonds. The ester may be formed, for example, by using a carbodiimide such as dicyclohexylcarbodiimide (DCC) according to known methods. The resulting activated ester is then combined with the desired poly(amino acid) in aqueous buffered medium at moderate temperature and the pH maintained and monitored during the addition of the ester to the poly(amino acid).

By employing the procedure of the present invention, PCP is functionalized to a compound which can be readily conjugated to poly(amino acid), either antigenic proteins or enzymes. The structure of the PCP is retained during the synthesis and those elements of the structure which provide for distinction between closely similar compounds are exposed to allow for formation of antibodies which are capable of clinically distinguishing PCP from structurally similar compounds, such as dextromethorphan, demerol and chlorpromazine.

The group Z is bonded to the linking group Y and may be a hydrogen, hydroxy, $C_{1-6}$ alkoxy groups or an oxy group forming an activated ester (when Y contains a carbonyl group bonded to Z) which reacts readily with the amine group of poly(amino acid)s in an aqueous medium to form amides. Preferred alkoxy groups are those having 1-3 carbon atoms, particularly methoxy and ethoxy groups. Preferred oxy groups forming activated esters are N-hydroxy-succinimide, p-nitrophenoxy or lower ($C_{1-6}$) alkyl-carboxy groups.

For derivatives in which Z is hydrogen, hydroxy, alkoxy or an oxy group forming an activated ester, n=1. When Z is a poly(amino acid), n ranges from 1 to the molecular weight of Z divided by 500, preferably the molecular weight of Z divided by 1,000, more preferably the molecular weight of Z divided by 1,500. In the embodiment where Z is an antigenic protein, n generally ranges from 1 to about 500, preferably 10-100. In the embodiment where Z is an enzyme, n generally ranges from 1 to about 30, preferably 2-20, more preferably 2-16.

The molecular weight of the poly(amino acid) will generally range upward from about 5,000 molecular weight, having no upper molecular weight limit, but normally being less than 10,000,000, and usually being not more than about 600,000. There may be different ranges depending on whether an antigen or an enzyme is used. With antigens, the range will be from about 5,000 to 10,000,000, usually from about 20,000 to 600,000, and more usually from about 25,000 to 250,000 molecular weight. With enzymes, the range will be from about 10,000 to 600,000, and more usually from about 10,000 to 300,000 molecular weight. For both antigens and enzymes, there will usually be at least about 1 PCP derivative group per 500,000 molecular weight, more usually at least one per 50,000 molecular weight. In the case of intermediate molecular weight antigens (35,000 to 600,000), the number of PCP derivative groups will generally be from about 2 to 250, more usually from 10 to 100. With lower molecular weight antigens (below 35,000), the number of PCP derivative groups will generally be in the range from about 2 to 10, usually in the range from 2 to 5.

Various protein types may be employed as the antigenic material. These types include albumins, serum proteins, e.g., globulins, ocular lens proteins, lipoproteins, etc. Illustrative proteins include bovine serum albumin, keyhole limpet hemocyanin, egg ovalbumin, bovine gamma-globulin, etc. Alternatively, synthetic poly(amino acids) may be prepared having sufficient available amino groups, e.g., lysines.

The enzymes may vary widely, depending on the ease of conjugation, turnover rate, and the physiological fluid in which the phencyclidine is to be measured. Preferably, the enzymes of choice, based on the I.U.B. classifications are: Class 1, Oxidoreductases and Class 3, hydrolases. Particularly in Class 1, the preferred enzymes are dehydrogenases of Class 1.1, more preferably, Sub-classes 1.1.1 and 1.1.99 and peroxidases in Class 1.11. Of the hydrolases, preferably Class 3.1, more preferably 3.1.3 and Class 3.2, more preferably 3.2.1.

Illustrative dehydrogenases include malate dehydrogenase, glucose-6-phosphate dehydrogenase, and lactate dehydrogenase. Illustrative peroxidases include horseradish peroxidase, and illustrative hydrolases include alkaline phosphatase, beta-galactosidase, beta-glucosidase and lysozyme.

Particularly preferred are those enzymes which employ nicotinamide adenine dinucleotide (NAD), or its phosphate (NADP) as a cofactor, preferably the former, or the reduced forms thereof. Illustrative of these enzymes is glucose-6-phosphate dehydrogenase.

The antigen conjugated may be injected into a wide variety of vertebrates in accordance with conventional methods for the production of antibodies. Usually the animals are bled periodically with successive bleeds having improved titer and specificity, until reaching a plateau and then diminishing in their specificity and titer. The antigens may be injected intramuscularly, intraperitoneally, subcutaneously, or the like. Usually a vehicle is employed, such as complete or incomplete Freund's adjuvant.

The antibodies and enzyme reagents prepared in accordance with the present invention find particular use in immunoassays for the determination of PCP in biological specimens. A description of the method for carrying out a homogeneous enzyme immunoassay may be found in U.S. Pat. No. 3,817,837 incorporated herein by reference. The method involves combining the enzyme conjugate, the unknown sample suspected of containing PCP, and an antibody for PCP in an aqueous buffered medium at temperatures in the range from about 10°-50° C., usually from about 20°-40° C.

Other features of the invention will become apparent in the course of the following descriptions of exemplary embodiments which are given for illustration of the invention and are not intended to be limiting thereof. Actual examples which have been reduced to practice are presented in the past tense. Examples which have been constructively reduced to practice are presented in the present tense.

EXAMPLES

Example 1

Preparation of 4-cyano-4-piperidino-cyclohexane ethylene ketal

1,4-Cyclohexanedione monoethyleneketal (7.81 g; 0.05 mole), potassium cyanide (3.9 g; 0.06 mole), and piperidine hydrochloride (7.3 g; 0.06 mole) were dissolved in 60 ml of 95% ethanol and 60 ml of water in a round bottom flask. The mixture was stirred at room temperature for 16–24 hours and the white precipitate was collected. The filtrate was concentrated under reduced pressure to give additional precipitate. The solid precipitate was combined to give 10.7 g (84% yield) of the desired product.

Example 2

Preparation of 4-phenyl-4-piperidinocyclohexane ethylene ketal

The ethylene ketal (2.5g; 0.01 mole) prepared in Example 1 was dissolved in 30 ml of anhydrous tetrahydrofuran (THF) under argon. The solution was vigorously stirred while 5 ml of phenyl magnesium bromide (3M in ether) was added. After addition, the mixture was stirred at room temperature overnight and saturated ammonium chloride (10 ml) was added slowly to the reaction mixture. The THF was removed under reduced pressure to give a solid residue. The residue was extracted with ether and the ether extracts were combined and dried over anhydrous sodium sulfate. The ether was removed under reduced pressure to give the desired phenyl derivative as an off-white solid (2 g; 67% yield).

Example 3

Preparation of 4-phenyl-4-piperidinocyclohexanone

The solid phenyl derivative of Example 2 (1.55 g; 5 mmole) was dissolved in 10 ml of 6 N HCl and the solution was allowed to stand at room temperature overnight. The acidic solution was carefully neutralized with solid sodium carbonate and extracted with ethyl ether. The ether extract was washed once with water and dried over anhydrous sodium sulfate. The ether was removed under reduced pressure to give a solid residue. The solid residue was recrystallized from hexane to give the desired cyclohexanone as a white crystalline (1.24 g; 94% yield).

Example 4

Preparation of 4-phenyl-4-piperidinocyclohexanol

The cyclohexanone derivative of Example 3 (1 g; 3.9 mmole) was dissolved in 50 ml of methanol inside a three-necked round bottom flask equipped with a condenser. 0.5 g of sodium borohydride was added portionwise to this solution. After addition, the mixture was stirred at room temperature for 2 hours. The methanol was removed under reduced pressure to give a solid residue. The solid residue was extracted with ethyl acetate. The ethyl acetate extracts were combined and washed once with water and dried over anhydrous sodium sulfate. Ethyl acetate was removed to give a solid material. The solid was recrystallized from hexane/ether (1:1; v/v) to give the desired cyclohexanol derivative as a white crystalline solid (0.89 g; 85% yield).

Example 5

Preparation of 4-Phenyl-4-Piperidinocyclohexylamine

4-Phenyl-4-(1-piperidino)cyclohexanone of Example 3 (0.95 g, 3.7 mmol) and ammonium acetate (4.3 g, 55 mmole) were dissolved in 30 ml of anhydrous methanol. Sodium cyanoborohydride (0.5 g, 8 mmole) was added to the mixture while stirring. The mixture was stirred at room temperature overnight and concentrated HCl was then added until a white precipitate was obtained. The precipitate was removed by filtration. The filtrate was concentrated under reduced pressure to give a solid residue. The residue was taken up in 100 ml of water and to the aqueous extract was added concentrated HCl to pH 2. The solution was extracted with ethyl ether to remove the unreacted starting material. The mixture was then stirred in an ice bath and sodium hydroxide was added until the solution pH reached 11. The mixture was then extracted with chloroform. The chloroform extract was washed once with water and dried over anhydrous sodium sulfate. Removal of chloroform under reduced pressure gave the desired cyclohexylamine in quantitative yield as a white solid.

Example 6

Acylation of 4-Phenyl-4-Piperidinocyclohexylamine

4-Phenyl-4-piperidino-cyclohexylamine (0.51 g, 2 mmole), succinic anhydride (0.25 g, 2.5 mmole) and a catalytic amount of triethylamine were dissolved in 20 ml of anhydrous DMF. The mixture was stirred at room temperature overnight. The solvent was removed under reduced pressure to give a solid residue. The solid residue was purified with thin layer chromatography to give the desired amino-acylated derivative (0.5 g, 80.9% yield) with a free carboxylic acid functional group.

Example 7

Preparation of Mercaotoacetic Acid Derivative of 4-Phenyl-4-Piperidino-cyclohexanone

4-Phenyl-4-piperidino-cyclohexanone (0.26 g, 1 mmole) was dissolved in 10 ml of ethyl ether at room temperature. The mixture was stirred at room temperature and mercaptoacetic acid (0.27 g, 2.5 mmole) was added. The cloudy solution slowly cleared up after four hours. The solvent and excess amount of mercaptoacetic acid were removed under reduced pressure to give an oil residue. The residue was purified with thin layer chromatography to give the di-thioketal derivative (0.2 g, 60% yield) of the cyclohexanone with free carboxylic acid functional groups.

Example 8

Preparation of ethyl ester of PCP-carbamate

The cyclohexanol derivative of Example 4 (1.2 g; 4.6 mmole) was dissolved in 25 ml of benzene inside a round bottom flask equipped with a Dean-Stark trap and the mixture was brought to reflux. The first 15 ml benzene distillate was removed. 0.5 ml of ethyl isocyanatoacetate was added to the remaining mixture. After addition, the mixture was refluxed for another 3 hours. After cooling to room temperature, the mixture was evaporated to give a heavy oil residue. The oil residue was extracted with ether and the undissolved material was removed by filtration. The organic ether solution was then extracted with 1 N HCl. The aqueous acidic extract was washed once with ether and evaporated to dryness under reduced pressure to give the desired PCP-carbamate derivative as a pale yellow solid (2.1 g; 87% yield).

Example 9

Preparation of ethyl ester of PCP-urethane

The ethyl ester of the PCP-urethane is prepared by reacting ethyl isocyanatoacetate with the cyclohexyl amine derivative of Example 5 following the procedure described in Example 8. Work-up provides the desired PCP-urethane derivative.

Example 10

Preparation of acid derivative of PCP-carbamate

The ethyl ester of PCP-carbamate hydrochloride (1.25 g; 2.95 mmole) was dissolved in 20 ml of methanol containing 3 ml of 6 N sodium hydroxide. The solution was then stirred at room temperature for 2 hours. The mixture was evaporated to dryness under reduced pressure to give a solid residue and the solid residue was taken up in methanol. The insoluble material was removed by filtration. The methanol was removed to give the desired PCP-carbamate acid derivative as a white solid (1.05 g; 91% yield).

Example 11

Preparation of acid derivative of PCP-urethane

In a matter analogous to Example 10, the ethyl ester of the PCP-urethane hydrochloride is hydrolyzed to give the corresponding PCP-urethane acid derivative.

Example 12

Preparation of PCP-bovine serum albumin (BSA) conjugate

The PCP-carbamate acid derivative of Example 10 (150 mg; 0.42 mmole), N-hydroxysuccinimide (65 mg; 0.57 mmole) and dicyclohexylcarbodiimide (103 mg; 0.51 mmole) were dissolved in 2 ml of anhydrous N,N-dimethylformamide. The mixture was stirred at refrigerated temperature overnight. A white precipitate formed and was filtered. The filtrate was added dropwise to an ice cold solution of BSA (500 mg) in 40 ml of 0.1 N carbonate buffer pH 9.0. After addition, the mixture was stirred at refrigerated temperature overnight followed by dialysis according to conventional procedure. Lyophilization of the mixture gave the desired PCP-BSA conjugate (545 mg) as a solid white powder.

Example 13

Preparation of 4-Phenyl-4-PiperidinoCyclohexylidenepropionic Acid

4-Phenyl-4-piperidino-cyclohexanone (0.257 g; 1 mmole) and β-carboxyethyltriphenylphosphonium chloride (0.371 g; 1 mmole) were dissolved in 20 ml of 1:1 DMSO-tetrahydrofuran and added to dry sodium hydride under nitrogen at 0° C. The reaction mixture was stirred at refrigerated temperature overnight. The solvent was removed under reduced pressure to give a solid residue. The solid residue was extracted with ethyl acetate. The acetate extracts were combined and washed once with water. After drying over anhydrous sodium sulfate, the solvent was evaporated to dryness to give the desired PCP cyclohexylidenepropionic acid as an off-white solid in 66% yield.

Example 14

Reduction of PCP Cyclohexylidenepropionic Acid

PCP cyclohexylidenepropionic acid (0.16 g; 0.5 mmole) was dissolved in 10 ml of anhydrous ethanol. To this mixture was added palladium/activated charcoal and the solution was placed in a hydrogenation apparatus. The system was first flushed with nitrogen followed by hydrogen and placed under a hydrogen atmosphere. The mixture was stirred at room temperature until the theoretical amount of hydrogen gas had been consumed. The activated charcoal was removed by filtration through a thin layer of celite. The solvent was removed to give the saturated PCP cyclohexylpropionic acid in almost quantitative yield.

Example 15

Preparation of PCP-G6PDH enzyme conjugate

Glucose-6-phosphate dehydrogenase (G6PDH) was dialyzed into 50 mM Tris buffer, pH 8.0 and adjusted to a concentration of 1 mg/ml. The solution was stirred in an ice bath and glucose-6-phosphate (5 mg/ml) was added. The activated PCP-carbamate acid derivative as prepared in Example 12 was added slowly and the deactivation of the G6PDH enzyme activity was monitored. The reaction was stopped when the enzyme activity was deactivated 40%. The G6PDH enzyme conjugate was purified by fractionation through a SEPHADEX G-25 column eluting with 50 mM Tris buffer, pH 8.0.

The compositions of the present invention provide reagents which provide a sensitive, accurate assay for phencyclidine, distinguishing phencyclidine from closely related metabolites which are encountered in samples. The antigenic conjugates provides for the efficient production of antibodies having high affinity and high titer for phencyclidine. The combination of the antibodies and enzyme conjugates result in an accurate rapid assay for phencyclidine in serum or urine.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A compound of the formula

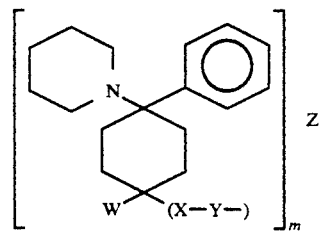

wherein:

Y is a bond or a linking group;

X is $(CH_2)_a$ where $a = 1$-$10$, NR where R is H, $C_{1-6}$ alkyl or said linking group Y, or S;

W is H or $C_{1-8}$ alkyl;

Z is hydroxy, $C_{1-6}$ alkoxy, an oxy group forming an activated ester reactive with amine groups of a poly(amino acid) or Z is a poly(amino acid);

m=1 when Z is hydroxy, alkoxy or said oxy group, and m is an integer from 1 to the molecular weight of Z divided by 500 when Z is a poly(amino acid).

2. The compound of claim 1, wherein X is $C_{1-6}$ alkylene.

3. The compound of claim 1, wherein X is NR where R is H or $C_{1-6}$ alkyl.

4. The compound of claim 3, wherein R is H.

5. The compound of claim 1, wherein X is S.

6. The compound of claim 1, wherein W is H.

7. The compound of claim 1, wherein W is $C_{1-8}$ alkyl.

8. The compound of claim 1, wherein Z is hydroxy or $C_{1-6}$ alkoxy.

9. The compound of claim 1, wherein Z is a poly(amino acid).

10. The compound of claim 1, wherein Z is an antigenic protein.

11. The compound of claim 1, wherein Z is an enzyme.

12. The compound of claim 11, wherein said enzyme is glucose-6-phosphate dehydrogenase.

13. The compound of claim 10, wherein Z is a globulin, an albumin or keyhole limpet hemocyanin.

14. The compound of claim 1, wherein said linking group Y contains a carbonyl group bonded to Z and Z is N-hydroxy succinimide, p-nitrophenoxy or lower alkyl carboxy.

15. The compound of claim 1, wherein said compound is 4-phenyl-4-piperidino-cyclohexylamine.

16. The compound of claim 1, wherein W is H, X is NH, Y is —C(O)—CH$_2$CH$_2$—COO, Z is H and m=1.

17. The compound of claim 1, wherein said compound is 4-phenyl-4-piperidino-cyclohexylidenepropionic acid.

18. A compound of the formula

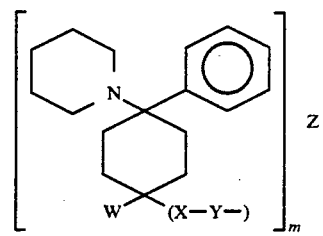

wherein:
X is O;
Y is C(O)—NR or C(O)—NR—R$^1$—C(O) where R is H, a straight-chain or branched $C_{1-10}$ alkyl group and R$^1$ is $C_{1-10}$ alkylene;
W is H or $C_{1-8}$ alkyl;
Z is a poly(amino acid); and
m is an integer from 1 to the molecular weight of Z divided by 500.

19. The compound of claim 18, wherein R is H.

20. The compound of claim 18, wherein W is H.

21. A compound of the formula:

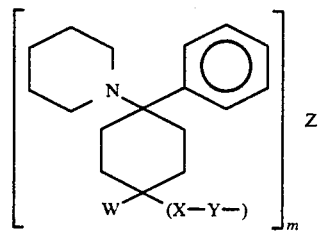

wherein:
X is NR where R is H or $C_{1-6}$ alkyl;
Y is C(O)—NR or C(O)—NR—R$^1$—C(O) where R is H, a straight-chain or branched $C_{1-10}$ alkyl group and R$^1$ is $C_1$ alkylene;
W is H or $C_{1-8}$ alkyl;
Z is a poly(amino acid); and
m is an integer from 1 to the molecular weight of Z divided by 500.

22. The compound of claim 21, wherein R and R$^1$ are hydrogen.

23. The compound of claim 21, wherein W is hydrogen.

* * * * *

UNITED STATES PATENT AND TRADEMARK OFFICE
CERTIFICATE OF CORRECTION

PATENT NO. : 5,304,479
DATED : April 19, 1994
INVENTOR(S) : Cheng-I Lin et al

It is certified that error appears in the above-indentified patent and that said Letters Patent is hereby corrected as shown below:

Column 2, line 15, "wherein is H" should read --wherein R is H--.

Column 3, line 40, "-O-C(O)-NR-" should read -- -C(O)-NR- --;
       line 45, "-P(P)(OR)" should read -- -P(O)(OR) --.

Column 12, line 40, $C_1$ alkylene" should read --$C_{1-10}$ alkylene--.

Signed and Sealed this

Thirtieth Day of August, 1994

Attest:

BRUCE LEHMAN

Attesting Officer    Commissioner of Patents and Trademarks